(12) United States Patent
Gester et al.

(10) Patent No.: US 10,229,549 B2
(45) Date of Patent: Mar. 12, 2019

(54) SYSTEM FOR AUTHORIZATION CONTROL AND BREATH TESTING

(71) Applicant: Senseair Alcohol Sensing AB, Västerås (SE)

(72) Inventors: Raimo Gester, Västerås (SE); Bertil Hök, Västerås (SE); Lars Tenerz, Uppsala (SE)

(73) Assignee: SENSAIR ALCOHOL SENSING AB, Västerås (SE)

( * ) Notice: Subject to any disclaimer, the term of this patent is extended or adjusted under 35 U.S.C. 154(b) by 0 days.

(21) Appl. No.: 15/437,664

(22) Filed: Feb. 21, 2017

(65) Prior Publication Data
US 2017/0243419 A1    Aug. 24, 2017

(30) Foreign Application Priority Data
Feb. 22, 2016    (SE) ........................... 1650227

(51) Int. Cl.
| | | |
|---|---|---|
| G05B 19/00 | (2006.01) |
| G05B 23/00 | (2006.01) |
| G06F 7/00 | (2006.01) |
| G06F 7/04 | (2006.01) |
| G06K 19/00 | (2006.01) |
| G08B 29/00 | (2006.01) |
| G08C 19/00 | (2006.01) |
| H04B 1/00 | (2006.01) |
| H04B 3/00 | (2006.01) |
| H04L 9/14 | (2006.01) |
| H04L 9/32 | (2006.01) |
| H04Q 1/00 | (2006.01) |
| H04Q 9/00 | (2006.01) |
| G07C 9/00 | (2006.01) |
| A61B 5/00 | (2006.01) |
| A61B 5/08 | (2006.01) |
| A61B 5/1172 | (2016.01) |
| A61B 5/1171 | (2016.01) |

(52) U.S. Cl.
CPC .......... *G07C 9/00158* (2013.01); *A61B 5/082* (2013.01); *A61B 5/4845* (2013.01); *A61B 5/0002* (2013.01); *A61B 5/1172* (2013.01); *A61B 5/1176* (2013.01); *A61B 2562/08* (2013.01)

(58) Field of Classification Search
CPC ...................... G07C 9/00158; A61B 5/4845
USPC ........................................................ 340/5.21
See application file for complete search history.

(56) References Cited

U.S. PATENT DOCUMENTS

| | | | |
|---|---|---|---|
| 8,529,462 B2 | 9/2013 | Crucilla | |
| 2010/0012417 A1* | 1/2010 | Walter | .................. B60K 28/063 180/272 |
| 2010/0204600 A1* | 8/2010 | Crucilla | .................. A61B 5/097 600/532 |
| 2013/0206495 A1* | 8/2013 | Westbrook | ........... B60K 28/063 180/272 |

(Continued)

*Primary Examiner* — Tanmay Shah
(74) *Attorney, Agent, or Firm* — Foley & Lardner LLP

(57) ABSTRACT

A system for authorization control and breath testing, comprising a management system unit and an authorization control and breath testing unit, wherein the authorization control and breath testing unit is configured to grant authorization to an individual seeking authorization without having access to any personal identification information about that individual.

19 Claims, 1 Drawing Sheet

(56) References Cited

U.S. PATENT DOCUMENTS

2015/0233897 A1     8/2015   Hok et al.
2016/0086021 A1*   3/2016   Grohman ........... G06K 9/00288
                                                                                   701/36

* cited by examiner

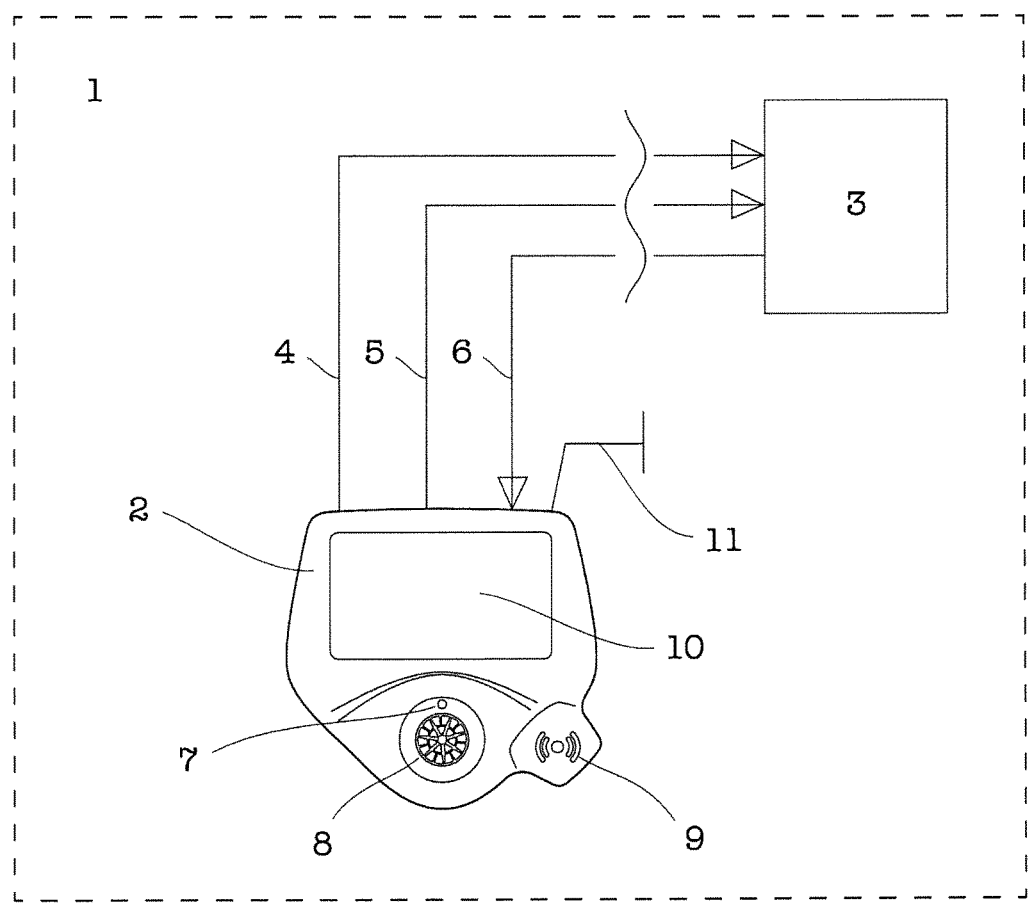

SYSTEM FOR AUTHORIZATION CONTROL AND BREATH TESTING

FIELD OF THE INVENTION

The present invention relates generally to a system for authorization control and breath testing, and in particular to a system comprising an authorization control and breath testing unit, into which a person enters authorization information and also delivers a breath sample, which the authorization control and breath testing unit analyzes to detect alcohol and/or one or several drugs, and a management system unit, in which personal identification information is stored, wherein the authorization control and breath testing unit grants authorization based on the authorization information and the result of the alcohol and/or drug analysis, and wherein the authorization information and the test result are sent from the authorization control and breath testing unit to the management system unit, which, via the authorization information, links the test result to the personal identification information and stores the test result together with the personal identification information.

BACKGROUND OF THE INVENTION

Today, it is common that a company or another institution, such as a school or a public building, not only wants to control authorization and access to its premises but also wants to ensure that the individuals who are about to enter the premises are free from influence of alcohol and other drugs. Systems and methods which can be used for this purpose are known. The U.S. Pat. No. 8,529,462 to Crucilla discloses an automated system and a method for passive testing of alcohol and drug abuse, wherein a testing device, which can be a home device or a kiosk device, enrolls a participant, validates biometrics information of this participant, conducts a test for alcohol and drug, and analyzes the test result for determining whether the participant has used alcohol or other drugs. Although such a system works well from a pure technical perspective, it causes problems when it is used in a public or semi-public environment. In a system wherein all data, i.e. both personal identification information and test result data, is contained in one physical unit, there is a potential risk that the personal integrity of the individuals whose identification information is stored in this physical unit is compromised. This can be the case if, for example, someone illegitimately retrieves the information stored therein. Also legitimate access, e.g. by a company which manufactures and/or performs maintenance functions on the physical units, can be in contradiction with national or international legislation regarding protection of personal data. An example of such legislation is the Data Protection Directive of the European Union (officially Directive 95/46/EC on the protection of individuals with regard to the processing of personal data and the free movement of such data).

Thus, there is a need for a system for combined authorization control and breath testing for alcohol and/or other drugs, which system guarantees the personal integrity of the individuals who are using and tested by the system.

SUMMARY OF THE INVENTION

The above-mentioned object is achieved by the present invention according to the independent claim. Preferred embodiments are set forth in the dependent claims.

In short, the present invention relates to a system for authorization control and breath testing, comprising a management system unit and an authorization control and breath testing unit, wherein the authorization control and breath testing unit is configured to grant authorization to an individual seeking authorization without having access to any personal identification information about that individual, thereby guaranteeing the personal integrity of the individuals using the system.

More specifically, the present invention relates to a system for authorization control and testing for alcohol and/or drugs in a breath sample provided by a person. The system comprises an authorization control and breath testing unit, which typically is placed in a public or semi-public environment, and a management system unit, which is kept in a safe and private environment, i.e. the authorization control and breath testing unit is typically and preferably placed remote from the management system unit, but the distance between the authorization control and breath testing unit and the management system unit is rather measured in terms of safety than in absolute length units, but a long distance between the two units can, of course, imply that it is more difficult to even localize where the management system unit actually is situated. The authorization control and breath testing unit implements an authorization control of a person who wishes to get some kind of authorization, and performs an analysis of a breath sample delivered by that person, to test whether the person in question is under influence of alcohol and/or some other drug. If the authorization control delivers a positive result, i.e. authorization information provided by the person seeking authorization matches with authorization data stored in the authorization control and breath testing unit, and if the alcohol and/or drug test delivers a negative result, i.e. no alcohol or other drugs are detected in the breath sample (or, if an amount of alcohol or some other drug actually is detected, then this amount is below a specified, predetermined level), the authorization control and breath testing unit grants authorization for the person. The authorization control and breath testing unit sends the results of the authorization control and the alcohol and/or drug test to the management system unit; or the authorization control and breath testing unit can store the results of the authorization control and the alcohol and/or drug test for later transfer to the management system unit. The latter can be the case if the communication between the authorization control and breath testing unit and the management system unit for some reason is interrupted. The management system unit stores personal identification information of all potential users of the system, and one of its basic functions is to link the data provided by the authorization control and breath testing unit to the personal identification information. By this set-up, no personal identification data is accommodated in the authorization control and breath testing unit, and any retrieval, be it legitimate or illegitimate retrieval, of data therefrom does not compromise the integrity of the persons who have used the system.

BRIEF DESCRIPTION OF THE DRAWINGS

FIG. 1 shows a schematic overview of a system for authorization control and breath testing for alcohol and/or other drugs according to the present invention.

DETAILED DESCRIPTION OF PREFERRED EMBODIMENTS

FIG. 1 illustrates an embodiment of a system 1 for authorization control and breath testing according to the present invention. The system 1 comprises an authorization control and breath testing unit 2 and a management system unit 3. In the embodiment shown in FIG. 1, the authorization control and breath testing unit 2 is connected to the management system unit 3 by a first line 4, in which results of an authorization control are sent from the authorization control and breath testing unit 2 to the management system unit 3, and a second line 5, in which results of a breath test for alcohol and/or other drugs are sent from the authorization control and breath testing unit 2 to the management system unit 3. The authorization control and breath testing unit 2 further includes a breath analyzer 7, and an authorization control device 8, which preferably consists of a radio frequency identification (RFID) sensor. This RFID sensor has the capability to detect an encoded card with a passive radio frequency resonator enabling wireless detection. The authorization control and breath testing unit 2 preferably includes a connector 9 to receive electric power from a mains supply (not shown in the figure). As an alternative or complement to the RFID sensor, a miniature camera 10 is positioned in close proximity to the breath analyzer 7, and provides real-time images of the view as seen from the breath analyzer 7. A touch screen 11 is preferably also included in the authorization control and breath testing unit 2 providing a two-way human-machine interface by which instructions to the user can be communicated, and, conversely, the user may provide information to the system.

In another embodiment of a system according to the invention (not shown in FIG. 1), all data, i.e. both results from an authorization control and results from a drug and/or alcohol test, is sent on a common line from an authorization control and breath testing unit to a management system unit. The system 1 comprises further a third line 6, which is utilized by the management system unit 3 to communicate with the authorization control and breath testing unit 2. Such communication can comprise commands about different modes of operation, e.g. to enter into test mode or service mode, state monitoring, re-programming of, e.g., drug analysis method, change of allowable test results limits, etc. In another embodiment of a system according to the invention (not shown in FIG. 1), also such communication is sent on a line which common for all communication between an authorization control and breath testing unit and a management system unit; or an existing line, such as line 4 or line 5 of the embodiment illustrated in FIG. 1, is employed for communication between a management system unit and an authorization control and breath testing unit regarding modes of operation and similar state-affecting or monitoring communications. In other embodiments of the invention, all communications are wireless communications, e.g. by WLAN or GSM, or a combination of wireless communication and communication by wire. Devices and systems for testing and analyzing a breath sample to detect presence of alcohol and other drugs are well-known in the art. A system that can be used and implemented in an authorization control and breath testing unit is, for example, the breath test system disclosed in the U.S. Published Application No. 20150233897, whose entire contents are incorporated herein by reference for the methods and devices disclosed therein.

There are many possible applications of a system for authorization control and breath testing system according to the present invention, and below the system will be described with reference to a non-limiting example. A possible application of a system for authorization control and breath testing is in a company which wants to ensure that individuals, typically employees, entering its premises both have authorization and are not under the influence of alcohol and/or a drug. In a basic design of the system, authorization and access to the premises can be controlled by the issue of a pass, e.g. an electronic card, to each one of the employees. An authorization control and breath testing unit, such as authorization control and breath testing unit 2 of FIG. 1, performs an authorization control in a first step by reading the information contained (stored) in the pass, which is inserted into, or otherwise read by, the authorization control and breath testing unit by the person who wants authorization to get access the premises. By reading the pass, the authorization control and breath testing unit identifies the number of the pass and compares this pass number with the numbers contained in an authorization list stored in the authorization control and breath testing unit. If the card number is among the numbers listed in the authorization list, potential authorization is granted. In a second step, the authorization control and breath testing unit asks the person seeking authorization to deliver a breath sample into a suitable device connected to or being an integral part of the authorization control and breath testing unit. The authorization control and breath testing unit analyses the breath sample, to detect alcohol and/or one or several drugs, such as marijuana, hashish, heroin, opium, cocaine, amphetamine, methamphetamine etc., as it is programmed to do. Based on the result of the alcohol and/or drug analysis in combination with a valid pass—the validity of which was determined in the first step —,the authorization control and breath testing unit grants authorization to the person who wants to enter the premises. In other words, if the alcohol and/or drug analysis indicates a value (or several values if more than one substance is tested) below a certain specified and predetermined limit, the person is granted authorization; and, on the other hand, if the alcohol and/or drug analysis indicate a value above the specified and predetermined limit, the person is refused to enter the premises, and is typically directed to a security officer, or some other personnel, who can perform a further investigation of the matter.

In normal operation, the authorization control and breath testing unit instantly sends the result of the authorization control and the alcohol and/or drug test to the management system unit, which, in turn, links these results to the personal identification information stored in the management system unit. By this instant transfer of results, the management system unit can immediately react on the information, if, for example, a certain individual, who now is seeking authorization, needs some special attention or special treatment. However, here it should be appreciated that the authorization control and breath testing unit can execute both the authorization control and the alcohol and/or drug test without being in immediate communication with a management system unit. This is particular advantage of the system according to the invention, since it means that the system is still functioning even if the communication between the authorization control and breath testing unit is interrupted. If there has been an interruption in the communication between the authorization control and breath testing unit and the management system unit, results from authorization control and breath testing are stored in the authorization control and breath testing unit until communication is established again, and these results can be sent to the management system unit. The authorization control and breath testing unit can therefore operate as an autonomous or stand-alone unit, which further can be separately powered, i.e. either by its own electrical connection to the mains supply, or by a battery. Even more importantly, it should be noted that no personal identification information is stored in the authorization control and breath testing unit. In the example given above, the authorization data was stored in the form of an authorization list containing the numbers of the passes that have been issued and given to the persons who potentially and presumably should have authorization to enter the premises. In more sophisticated embodiments of the invention, authorization data can be provided in other forms, e.g. in the form of fingerprints, facial images or eyes identification. The important fact is that an authorization control and breath testing unit only stores such information as pictures, or rather pixels, and that there is no personal identification information stored in the authorization control and breath testing unit. Thus, even if an authorization control and breath testing unit is stolen and physically removed, there is no personal identification information contained therein, which could be retrieved and used for criminal, malicious or otherwise unauthorized purposes. Also, a company, which has manufactured an authorization control and breath testing unit or performs service on such unit, can have an interest in retrieving authorization control data or, more likely, drug test data, to check the performance and functionality of the authorization control and breath testing unit. Such a company has typically no interest in retrieving information about the individuals who have used the system, but can still be liable if the personal information is used in a way that is detrimental to some individual(s). Further, the mere possession of such personal data can be regarded as a criminal act, as was discussed above.

Although an authorization control and breath testing unit according to the invention operates as an autonomous and stand-alone device when it comes to permitting (or denying) the immediate authorization. However, a system for authorization control and breath testing has usually further functions. The company or another institution which installed and operates the system typically wants to retrieve information from an authorization control and breath testing unit. An important feature of the system for authorization control and breath testing is that personal identification information is not part of authorization information (although the management system unit can link the two types of information to each other and can store them together), because authorization information is contained or stored in the authorization control and breath testing unit whereas personal identification information is not stored in the authorization control and breath testing unit and the authorization control and breath testing unit has no access to the personal identification information. Such information is used to monitor which individuals reside within a certain area or premises, and, for example, to check which employees have come to their job a certain day and at what time. Also indications of alcohol and/or drug use may be monitored as warning signs that actions should be taken. To accomplish this, a management system unit according to the invention stores personal identification information together with authorization information, and is able to link and store the personal identification information to authorization results provided by or obtained from an authorization control and breath testing unit. The management system unit can duplicate all information contained therein, to, for example, ensure that a backup copy exists, which further can be stored in separate place, in case of total system failure or deletion of data. In a basic embodiment, the personal identification information is the name of an individual and the authorization information is the number of a pass issued to the individual; and the authorization results from the authorization control and breath testing unit is date and time when the individual was seeking authorization together with results from the alcohol and/or drug analysis, either only as "passed" or "denied", i.e. the results were below or above a predetermined limit, or in the form of actual measurement values. In more sophisticated embodiments, the authorization information can be provided in the form of fingerprints, facial images or eyes identification, etc., or the authorization information can be stored in a mobile phone or on other types of devices. In a system according to the invention, the cross-reference between authorization results and personal identification information is only done in a management system unit, and is not done, and cannot be done, in an authorization control and breath testing unit, since the authorization control and breath testing unit has no access to the personal identification information. Although a management system unit normally does not participate in the determination whether an individual seeking authorization should be granted such authorization, there is nevertheless typically a need for the management system unit to be in communication with an authorization control and breath testing unit. Such communication can be information about updates in the authorization information stored in the authorization control and breath testing unit, e.g. entry of new pass numbers (fingerprints, facial images or eyes identifications) or deletion of obsolete pass numbers (fingerprints, facial images or eyes identifications).

Communication from a management system unit to an authorization control and breath testing unit can also consist of commandos about mode of operation, e.g. switching from normal operation to different test or service modes, or re-programming or change of analysis method, or other types of status checks, or the specified limit below which a certain test result is acceptable (i.e. authorization is granted) can be changed. Such communication may or may not require answer from the authorization control and breath testing unit.

Although the present invention has been described with reference to specific embodiments, also shown in the appended drawings, it will be apparent to those skilled in the art that many variations and modifications can be done within the scope of the invention as described in the specification and defined with reference to the claims below. In particular, as used herein, the term "authorization" shall be given the broadest possible interpretation and shall, for example, encompass granting of physical access, such as physical access to an area or a premises or a building. The term "authorization" as used herein shall also encompass non-physical access, e.g. an authorization that an individual, such as an employee, is permitted to start working, e.g. start to operate a certain machinery or to drive a vehicle. The term "authorization" shall also encompass authorization of participation in, for example, a drug abuse testing program which an individual has previously enrolled. In the latter case, no physical access is granted, but the individual confirms further participation in the program by using the system for authorization control and breath testing.

The invention claimed is:

1. A system for authorization control and breath testing, comprising:
    a management system unit, in which personal identification information and authorization information is stored, and
    an authorization control and breath testing unit, in which authorization information is stored, the authorization control and breath testing unit being located in a location remote from a location of the management system unit and having no access to the personal identification information, wherein the authorization control and breath testing unit is configured to compare authorization data provided by an individual seeking authorization with the authorization information, the authorization control and breath testing unit is configured to analyze a breath sample provided by the individual seeking authorization and to detect the presence of alcohol and/or one or more drugs, the authorization control and breath testing unit is configured to grant authorization based on
  a positive match between the authorization data provided by the individual seeking authorization and the authorization information, and
  no detection of alcohol and/or other drug, or detection of an amount of alcohol and/or other drug which is below a specified limit, the authorization control and breath testing unit is configured to send results of a matching of authorization data and authorization information and results of an analysis of the breath sample to the management system unit, and the management system unit is configured to store results of the matching of authorization data and authorization information and results of the analysis of the breath sample and to link these results to the personal identification information, wherein the authorization control and breath testing unit is configured to, if communication between the management system unit and the authorization control and breath testing unit is interrupted,
  store the results of the matching of authorization data and authorization information and/or the results of the analysis of the breath sample; and
  send the stored results of the matching of authorization data and authorization information and/or the results of the analysis of the breath sample to the management system unit when communication between the management system unit and the authorization control and breath testing unit is reestablished.

2. The system according to claim 1, wherein the authorization control and breath testing unit is a self-powered unit.

3. The system according to claim 1, wherein the communication between the authorization control and breath testing unit and the management system unit is wired communication.

4. The system according to claim 1, wherein the communication between the authorization control and breath testing unit and the management system unit is wireless communication.

5. The system according to claim 1, wherein the authorization control and breath testing unit comprises a breath analyzer.

6. The system according to claim 1, wherein the authorization control and breath testing unit comprises an authorization control device.

7. The system according to claim 6, wherein the authorization control device comprises a radio frequency identification (RFID) sensor.

8. The system according to claim 6, wherein the authorization control device comprises a camera.

9. The system according to claim 8, wherein the camera provides real-time images of a view seen from the authorization control and breath testing unit.

10. The system according to claim 1, wherein the authorization control and breath testing unit comprises a touch screen, which provides a two-way human-machine interface for communication between a user and the system.

11. The system according to claim 1, wherein
the authorization control and breath testing unit is configured to analyze the breath sample provided by the individual seeking authorization and to detect the presence of one or more drugs, and
the one or more drugs comprise marijuana, hashish, heroin, opium, cocaine, amphetamine, methamphetamine or a combination thereof.

12. The system according to claim 1, wherein the authorization control and breath testing unit is configured to, if communication between the management system unit and the authorization control and breath testing unit is not interrupted, instantly send the results of the matching of authorization data and authorization information and/or the results of the analysis of the breath sample to the management system unit.

13. The system according to claim 1, wherein the management system unit and the authorization control and breath testing unit are separately powered.

14. A system for authorization control and breath testing, comprising:
  a management system unit, in which personal identification information and authorization information is stored, and
  an authorization control and breath testing unit, in which authorization information is stored, the authorization control and breath testing unit being located in a location remote from a location of the management system unit and having no access to the personal identification information, wherein
  the authorization control and breath testing unit is configured to compare authorization data provided by an individual seeking authorization with the authorization information,
  the authorization control and breath testing unit is configured to analyze a breath sample provided by the individual seeking authorization and to detect the presence of alcohol and/or one or more drugs,
  the authorization control and breath testing unit is configured to grant authorization based on
    a positive match between the authorization data provided by the individual seeking authorization and the authorization information, and
    no detection of alcohol and/or other drug, or detection of an amount of alcohol and/or other drug which is below a specified limit,
  the authorization control and breath testing unit is configured to send results of a matching of authorization data and authorization information and results of an analysis of the breath sample to the management system unit, and
  the management system unit is configured to store results of the matching of authorization data and authorization information and results of the analysis of the breath sample and to link these results to the personal identification information, wherein
  the authorization control and breath testing unit comprises an authorization control device,
  the authorization control device comprises a camera, and
  the camera provides real-time images of a view seen from the authorization control and breath testing unit.

15. The system according to claim 14, wherein the authorization control and breath testing unit is a self-powered unit.

16. The system according to claim 14, wherein the authorization control and breath testing unit comprises a touch screen, which provides a two-way human-machine interface for communication between a user and the system.

17. The system according to claim 14, wherein
the authorization control and breath testing unit is configured to analyze the breath sample provided by the individual seeking authorization and to detect the presence of one or more drugs, and
the one or more drugs comprise marijuana, hashish, heroin, opium, cocaine, amphetamine, methamphetamine or a combination thereof.

18. The system according to claim 14, wherein the authorization control and breath testing unit is configured to instantly send the results of the matching of authorization data and authorization information and/or the results of the analysis of the breath sample to the management system unit.

19. The system according to claim 14, wherein the management system unit and the authorization control and breath testing unit are separately powered.

\* \* \* \* \*